United States Patent
Koh

(10) Patent No.: US 7,413,549 B1
(45) Date of Patent: Aug. 19, 2008

(54) DETECTING AND QUANTIFYING APNEA USING VENTILATORY CYCLE HISTOGRAMS

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 772 days.

(21) Appl. No.: 10/803,449

(22) Filed: Mar. 17, 2004

(51) Int. Cl.
*A61B 5/08* (2006.01)

(52) U.S. Cl. .................. 600/529; 600/538; 600/484

(58) Field of Classification Search ......... 600/529–543, 600/481, 483, 484, 504–527
See application file for complete search history.

(56) References Cited

U.S. PATENT DOCUMENTS

| | | | | |
|---|---|---|---|---|
| 5,206,807 | A * | 4/1993 | Hatke et al. | 600/484 |
| 5,765,563 | A * | 6/1998 | Vander Schaaf | 600/538 |
| 6,223,064 | B1 * | 4/2001 | Lynn et al. | 600/324 |
| 6,306,088 | B1 * | 10/2001 | Krausman et al. | 600/301 |
| 6,342,039 | B1 * | 1/2002 | Lynn et al. | 600/529 |
| 6,454,719 | B1 | 9/2002 | Greenhut | 600/484 |
| 6,748,252 | B2 * | 6/2004 | Lynn et al. | 600/323 |
| 6,760,608 | B2 * | 7/2004 | Lynn | 600/324 |
| 6,881,192 | B1 * | 4/2005 | Park | 600/529 |
| 2005/0119711 | A1 * | 6/2005 | Cho et al. | 607/42 |

FOREIGN PATENT DOCUMENTS

| | | |
|---|---|---|
| EP | 1177764 A2 | 2/2002 |
| WO | WO 02/40096 A1 | 5/2002 |

* cited by examiner

*Primary Examiner*—Robert L. Nasser, Jr.
*Assistant Examiner*—Navin Natnithithadha

(57) ABSTRACT

Subject matter includes methods and devices for detecting and quantifying apnea. One exemplary implementation includes deriving a ventilation related parameter in real-time from a patient, deriving apneic intervals based on the parameter, distributing the apneic intervals as counts on a histogram, and calculating a single data point, such as a centroid, for clustered counts on the histogram. Centroids can be calculated at regular intervals and stored for lengthy periods, such as months, because they occupy very little storage space. A position of a centroid on the histogram can indicate an aspect of the patient's health and changes in the centroid positions over time can be used to detect trend changes in the patient's condition.

15 Claims, 12 Drawing Sheets

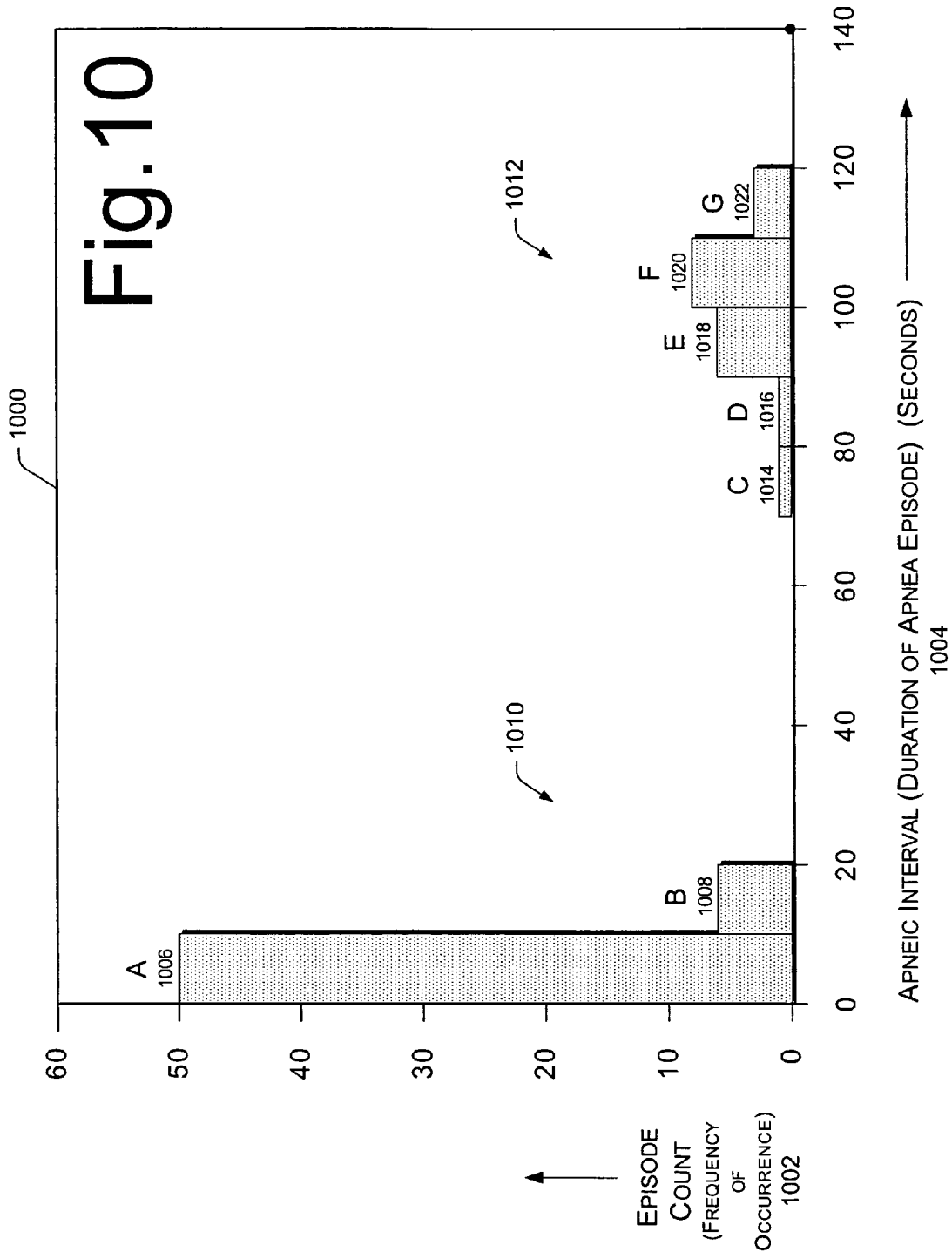

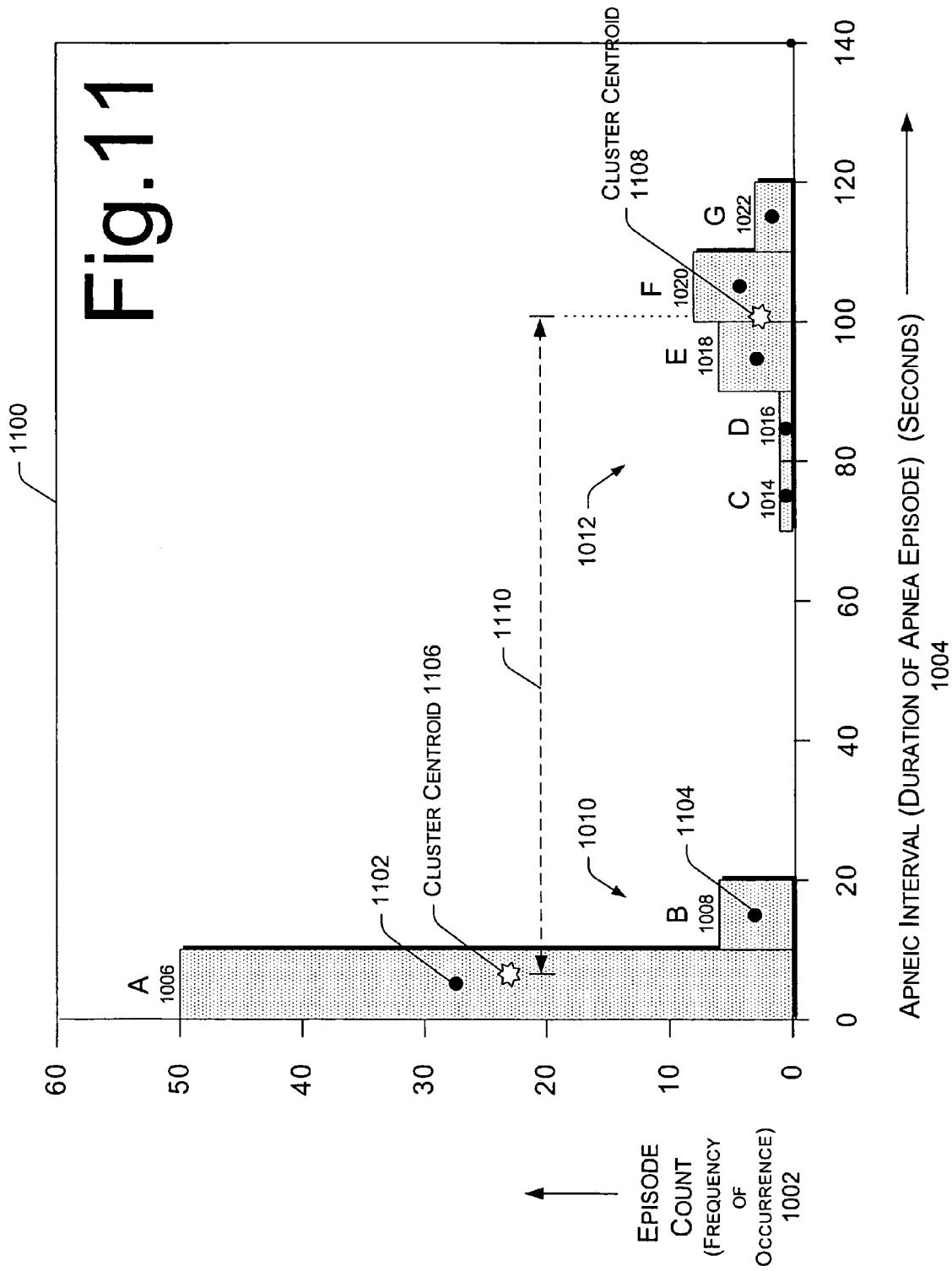

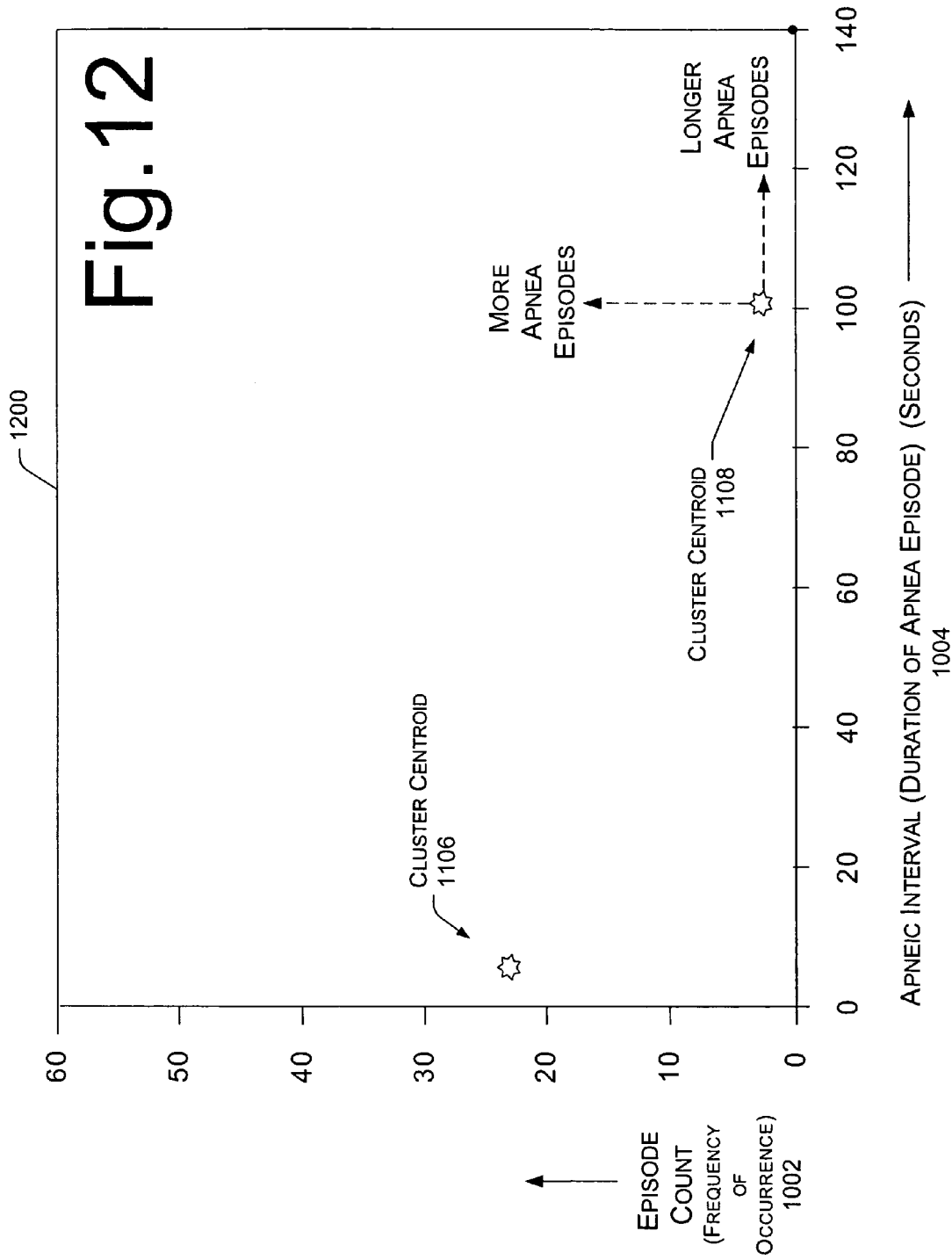

DETECTING AND QUANTIFYING APNEA USING VENTILATORY CYCLE HISTOGRAMS

TECHNICAL FIELD

The present invention relates generally to implantable devices, and more particularly, to detecting and quantifying apnea using ventilatory cycle histograms.

BACKGROUND

Human respiration consists of mechanical ventilation and capillary gas exchange. Mechanical ventilation refers to the ventilatory cycle of breathing, that is, the inspiration and expiration (or inhalation and exhalation) of air, which will be referred to herein as the ventilatory "cycle." Gas exchange refers to the exchange of oxygen and carbon dioxide between the lungs and the bloodstream.

Sleep apnea, a prevalent sleep disorder, manifests many ventilatory cycle disorders and other undesirable symptoms that range from snoring, breathing cessation, and headaches to depression, memory loss, and exacerbation of heart disease. "Hypopnea," a related malady that begets some of the same symptoms as apnea, refers to a breathing rate or tidal volume that is less than approximately fifty percent of a patient's normal baseline breathing pattern. The term "apnea" is often applied loosely to refer to any combination of sleep apnea and hypopnea.

It can be difficult to properly detect apnea and hypopnea, quantify their occurrence, and respond to long-term trend changes in these maladies. Implantable devices are generally not equipped with the pattern recognition capability, computational power, and memory to properly diagnose and efficiently store long-term apnea and hypopnea data gathered in raw form from a host patient. Apnea manifests itself as a complex and variable pathology that conventionally requires great computational intensity to automatically monitor and treat.

Blood chemistry changes occur when apnea and hypopnea modify normal breathing during sleep. Breathing difficulty can cause blood oxygenation to fall to low levels and carbon dioxide and its derivatives to build up in the blood. When respiratory control centers in the brain sense these chemical changes, they often direct an arousal of the apneic patient. Thereafter, regular breathing and normal exchange of oxygen and accumulated carbon dioxide may resume—for a time—until the next episode. Severe apnea and hypopnea can result in hundreds of episodes of low blood oxygen levels per night. The typical apnea patient may have little awareness of the nightly struggle to breathe until its effects are felt the next day.

Sleep apnea can be classified as "obstructive" if caused by mechanical blockage of airflow, "central" if caused by a central nervous system disorder, and "mixed" if it is a combination of the obstructive and central types.

Sleep apnea can be life-threatening if it occurs with coronary artery disease (CAD) or congestive heart failure (CHF—sometimes referred to as just "heart failure"). CHF is a condition in which a weakened heart cannot provide enough pressure to prevent buildup of fluid in bodily tissues. CHF may affect either the right side, left side, or both sides of the heart. The weak pumping action causes fluid to back up into other areas of the body including the liver, gastrointestinal tract, and extremities (right-sided heart failure), or the lungs (left-sided heart failure). Heart failure patients have characteristic pulmonary edema or pitting edema of the lower legs.

Structural and functional causes of heart failure include high blood pressure (hypertension), valvular heart disease, congenital heart disease, cardiomyopathy, heart tumor, and other heart diseases. Precipitating and exacerbating factors include infections with high fever, anemia, irregular heartbeats (arrhythmias), hyperthyroidism, and kidney disease, and of course, sleep apnea. CHF and sleep apnea often occur together in a patient, as mentioned above, and they make each other worse. Treating one usually improves the other.

Not only does apnea place a load on the heart and cardiopulmonary system directly, but indirectly affects these organs by circumventing restful sleep. Sleep debt and daytime weariness resulting from the apnea worsen CAD, CHF, and hypertension. Consequently, sleep apneics who have a blood oxygen level lowered by sleep-disordered breathing are at increasing risk for hypertension, arrhythmias, heart attack, and stroke.

Approximately fifty percent of patients with heart failure suffer concurrent sleep apnea. About ten percent of these heart failure patients suffer from obstructive sleep apnea, while about forty percent suffer from central sleep apnea. A high comorbidity exists between sleep apnea and CHF, which results from a negative synergy between problematic gas exchange during apnea and problematic oxygen distribution characteristic of CHF.

It is generally believed that reducing heart failure symptoms reduces apnea, which in turn further reduces the heart failure symptoms. Therapy administered by an implantable device for diagnosing and treating sleep apnea is still relatively unexplored. Hence, there is a continuing need to improve the techniques for detecting and quantifying apnea while conserving the memory and computational resources of an implantable device.

SUMMARY

Methods and implantable devices for detecting and quantifying apnea using ventilatory cycle histograms are described. One exemplary implementation includes deriving a ventilation related parameter in real-time from a patient, deriving apneic intervals based on the parameter, distributing the apneic intervals as counts on a histogram, and calculating a single data point, such as a centroid, for clustered counts on the histogram. Centroids can be calculated at regular intervals and stored for lengthy periods, such as months, because they occupy very little storage space. A position of a centroid on the histogram can indicate an aspect of the patient's health and changes in the centroid positions over time can be used to detect trend changes in the patient's condition.

BRIEF DESCRIPTION OF THE DRAWINGS

FIG. 10 is a graphical representation of an exemplary histogram of apneic intervals.

FIG. 11 is a graphical representation of an exemplary method for calculating histogram cluster centroids representing apneic intervals.

FIG. 12 is a graphical representation of exemplary centroid movement for tracking patient health.

DETAILED DESCRIPTION

Overview

Figure 1:
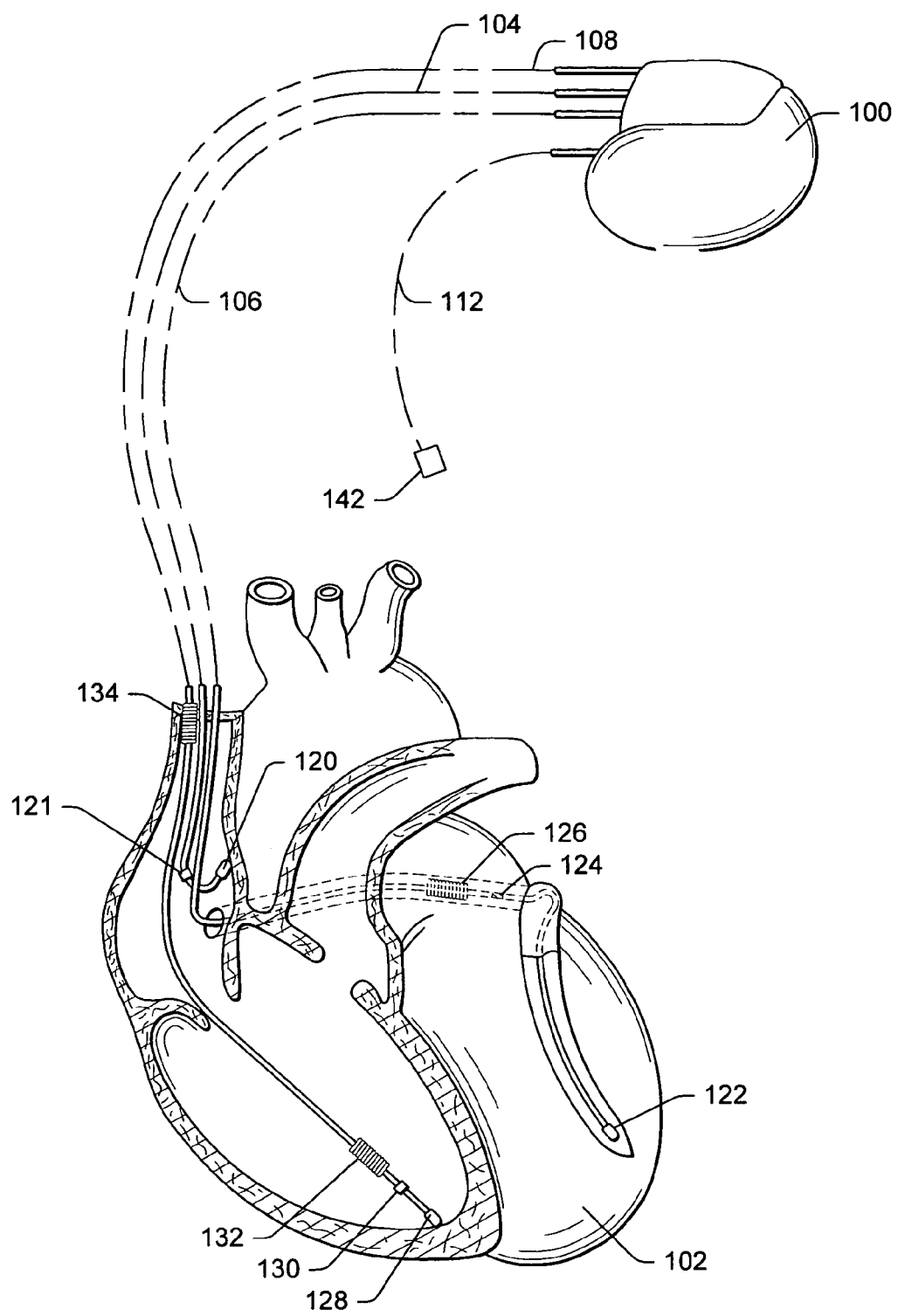
FIG. 1 is a diagrammatic illustration of an implantable device in electrical communication with a patient's heart for detection and quantification of apnea and for multi-chamber sensing and delivery of multi-chamber stimulation.

The subject matter described herein includes exemplary methods and devices for detecting and quantifying apnea using ventilatory cycle histograms. The exemplary methods can be performed in real-time and use less memory and computational power than conventional "in vitro" methods that include, for example, time-series trend analyses performed by a computer external to the patient's body. Using stored data derived from exemplary histograms, the subject matter allows an implantable device to provide ongoing long-term and short-term information about the progression of a patient's cardiopulmonary condition. This benefits the treatment of apnea and can also benefit a congestive heart failure (CHF) condition since the progression of a patient's apnea often parallels the patient's cardiac condition. The number and duration of apneic episodes within a timeframe as well as changes in trend can be provided to a practitioner or used within an implantable device to trigger respiratory or cardiac treatment algorithms or other correctives.

The subject matter provides an ongoing record of the patient's respiratory (and cardiac) health by condensing an ongoing history into a reduced amount of data via exemplary methods of data analysis and partitioning. In a first type of data partitioning, an exemplary method can detect bimodality between intervals of normal breathing and intervals of apnea. Individual ventilatory cycles are rated based on their tidal volume. By filtering the ventilatory cycles associated with normal intervals of breathing from the ventilatory cycles associated with apneic intervals of breathing, the exemplary method can determine the durations of apneic episodes, e.g., by measuring the time from the end of one interval of normal breathing to the beginning of the next interval of normal breathing.

In another type of data partitioning, the subject matter capsulizes respiratory data for efficient storage and for detection of trend changes over a multiple iterations of a timeframe. The alternating intervals of apnea and normal breathing can be tracked in a single histogram, which in one implementation can be configured as a type of "bar chart." An exemplary histogram includes classes or "bins"—the "bars" of the bar chart—each representing a range of time intervals, i.e., durations, of apnea episodes. One bin, for example, might represent the patient's apnea episodes that lasted between forty and fifty seconds in duration. When the end of an apnea episode is detected by an exemplary method described in more detail below, a corresponding bin on the histogram is incremented by one. Thus, in real-time or near real-time, an exemplary histogram can provide a great deal of information conveniently and compactly, such as the apnea duration most frequently experienced by a patient and the frequency distribution of the durations of multiple apnea episodes.

The durations of numerous apnea episodes tend to result in a characteristic cluster of bins on an exemplary histogram, since the durations of apnea episodes, at least for a given patient, tend to fall in a limited range. Likewise, brief pauses in breathing that are deemed normal also tend to result in a second cluster of bins on an exemplary histogram. The subject matter makes further use of these two types of clusters for diagnosis and tracking of trend changes in a patient's apnea over time.

The subject matter accomplishes diagnosis and trend tracking by selecting regular time intervals ("timeframes") for performing cluster analysis on an ongoing histogram. Timeframe selection is not limited, hence a timeframe can be an hour, a rest period, a 24-hour period, a month, etc. During cluster analysis, an exemplary method calculates a centroid for each cluster of the apnea episode durations distributed on the histogram. Each centroid can be thought of as a "center of mass" value for representing the average duration of apnea episodes that have been counted in a cluster either since the last cluster analysis or, in some implementations, since the beginning of tracking a particular patient.

Likewise, an exemplary method can also calculate a centroid value that represents the distributed durations of breathing pauses too brief to be apneic. The time interval between these two types of centroids (the apneic and the "normal" centroids) can be used to diagnose whether pauses in a patient's breathing really constitute apnea by current standards. The time interval(s) between centroids can also be used in some circumstances to form more specific diagnoses, such as a diagnosis of Cheyne-Stokes syndrome.

In one implementation, the selected timeframe for performing cluster analysis on an exemplary histogram is once every 24-hours, that is, daily. A "snapshot" of an ongoing histogram can be stored daily for comparison with preceding and succeeding snapshots of the histogram. This storage requires minimal data as each exemplary histogram is already a compact summary of breathing data.

In the same or another implementation, only one or more centroids are stored for each timeframe, e.g., daily, instead of or in addition to a snapshot of an entire exemplary histogram. Storing a first centroid representing durations of apnea episodes and a second centroid representing durations of brief normal breathing pauses requires even less data storage than a snapshot of an entire exemplary histogram, and storage of the two centroids implicitly stores the time interval between them.

In the same or another implementation, only the time interval between centroids is stored, if this is the only metric of interest for a given patient. For example, a patient may have reached a long-term baseline, and only daily or weekly intervals between centroids are stored for preventative maintenance, to detect a change in a long-term trend.

Regardless of which breathing information described above is selected for long term storage, the stored information can be retrieved and compared. For example, various centroid values can be compared to detect if one of the centroids is moving over the span of a week or a month. This allows a practitioner or implantable device to ascertain whether apnea and related heart conditions are improving or deteriorating. Thus, one or more histogram centroids properly derived according to exemplary methods described herein provide an elegant way to signal trend changes in a patient's health using reduced implantable device memory and computational power.

Exemplary Device

An implantable device, such as an exemplary device 100 shown in FIG. 1, may be programmed to perform the exemplary methods described herein, that is, to detect and quantify apnea in a patient, as well as to administer cardiac pacing therapy, if needed.

Once apnea is detected and/or quantified, a particular treatment regimen suited to the identified condition may also be selected by an exemplary device 100.

An exemplary device 100 can be characterized as a miniature computing device that is implanted into the body of a patient to monitor, regulate, and/or correct cardiac and other activity. Such devices include implantable cardiac stimulation devices (e.g., implantable cardiac pacemakers, implantable defibrillators) that apply stimulation therapy to the heart. The following discussion describes an exemplary device 100 that is effective for treating heart conditions, such as those related to heart failure, and for detecting and quantifying sleep apnea.

FIG. 1 shows the exemplary device 100 in electrical communication with a patient's heart 102 for monitoring cardiac activity, delivering stimulation therapy, such as pacing therapies, and for detecting and quantifying apnea. Three leads—a right atrial lead 104, a coronary sinus lead 106, and a right ventricular lead 108—interconnect the exemplary device 100 with the patient's heart 102 to support multi-chamber detection and stimulation therapy.

The right atrial lead 104 supports an atrial tip electrode 120, which typically is implanted in the patient's right atrial appendage. The right atrial lead 104 also supports a right atrial ring electrode 121, which enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the exemplary device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 may be used for shocking therapy.

The right ventricular lead 108 is electrically coupled to a right ventricular tip electrode 128, a right ventricular ring electrode 130, a right ventricular (RV) coil electrode 132, and a superior vena cava (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

A ventilation probe lead 112 is optionally positioned to facilitate measurement of a patient's ventilatory cycles. Since there are many ways to measure ventilatory cycles, placement depends on the ventilatory cycle probe 142 selected. For instance, if the ventilation cycle probe 142 is a mechanical movement sensor, then the ventilatory probe lead 112 usually terminates near a lung or near the diaphragm muscle.

Figure 2:
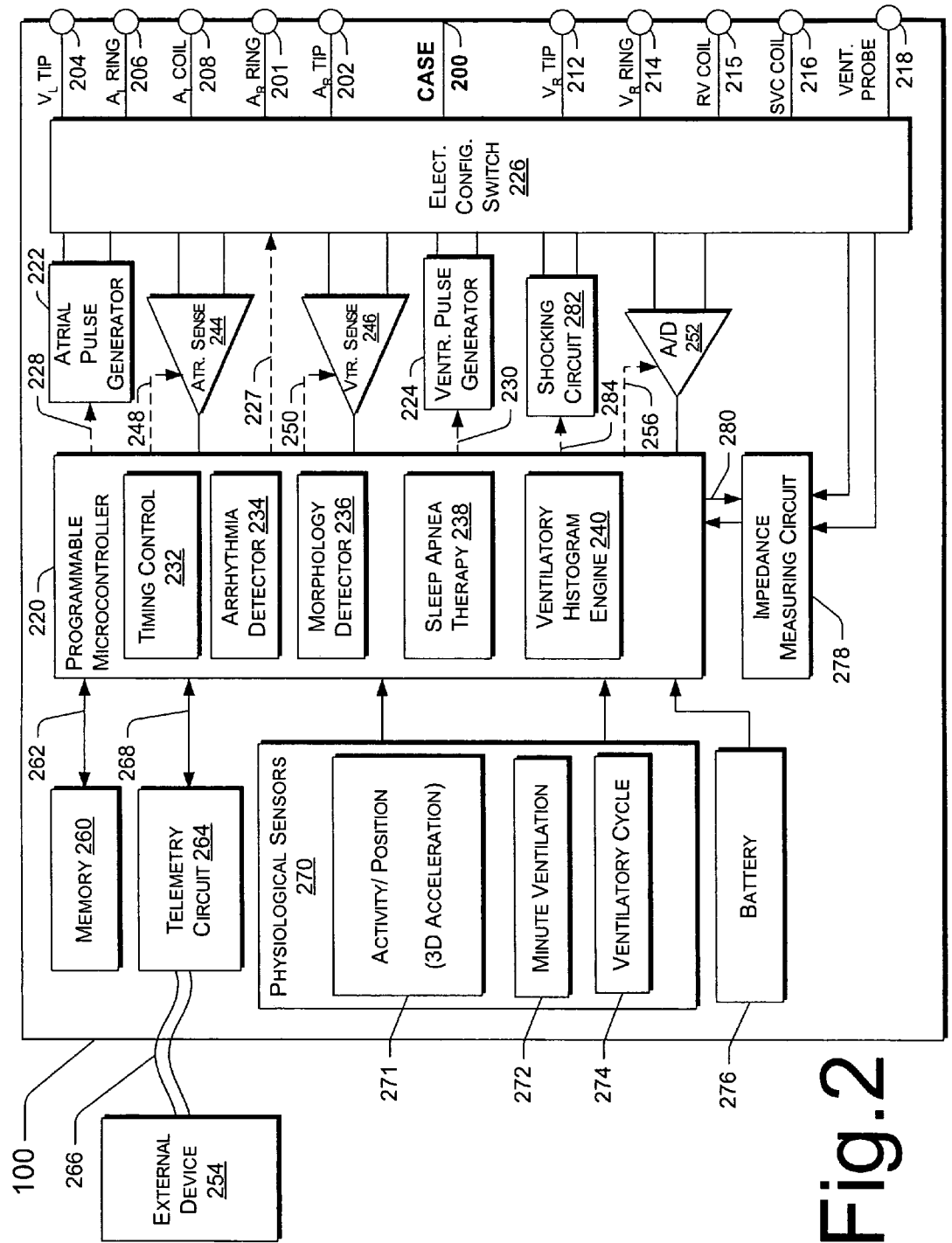
FIG. 2 is a functional block diagram of the implantable device of FIG. 1, including a ventilatory histogram engine.

FIG. 2 shows an exemplary block diagram depicting various components of an exemplary device 100. The components are contained in a case 200, which is often referred to as the "can", "housing", "encasing", or "case electrode", and may be programmably selected to act as the return electrode for unipolar operational modes. The case 200 may further be used as a return electrode alone or in combination with one or more of the coil electrodes 126, 132 and 134 for stimulating purposes. The case 200 further includes a connector (not shown) having a plurality of terminals (201, 202, 204, 206, 208, 212, 214, 215, 216, and 218—shown schematically with the names of the electrodes to which they are connected shown next to the terminals), including:

a right atrial ring terminal ($A_R$ RING) 201 for atrial ring electrode 121;

a right atrial tip terminal ($A_R$ TIP) 202 for atrial tip electrode 120;

a left ventricular tip terminal ($V_L$ TIP) 204 for left ventricular tip electrode 122;

a left atrial ring terminal ($A_L$ RING) 206 for left atrial ring electrode 124;

a left atrial shocking terminal ($A_L$ COIL) 208 for left atrial coil electrode 126;

a right ventricular tip terminal ($V_R$ TIP) 212 for right ventricular tip electrode 128;

a right ventricular ring terminal ($V_R$ RING) 214 for right ventricular ring electrode 130;

a right ventricular shocking terminal (RV COIL) 215 for RV coil electrode 132;

an SVC shocking terminal (SVC COIL) 216 for SVC coil electrode 134; and a ventilation probe terminal 218 for ventilation cycle probe 142.

An exemplary device 100 may include a programmable microcontroller 220 that controls various operations of the implantable cardiac device, including cardiac monitoring and stimulation therapy. Microcontroller 220 includes a microprocessor (or equivalent control circuitry), RAM and/or ROM memory, logic and timing circuitry, state machine circuitry, and I/O circuitry.

Exemplary device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The electrode configuration switch 226 may include multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 220 may also be equipped with an arrhythmia detector 234, a morphology detector 236, an optional sleep apnea therapy module 238, and a ventilatory histogram engine 240.

The sleep apnea therapy module 238 applies appropriate sleep apnea pacing therapy and/or respiratory therapy based on a programmed default and/or based on the detection and/or quantification of sleep apnea made by the ventilatory histogram engine 240.

The ventilatory histogram engine 240, which will be discussed more fully with respect to FIG. 3 below, derives a ventilatory cycle related parameter, calculates apneic intervals from the parameter, and distributes the apneic intervals as counts on a histogram. The ventilatory histogram engine 240 can also condense apneic intervals counted on the histogram into one or more single data points, or centroids, in order to store the apnea information efficiently and in order to track long range trends in a patient's conditions.

The components 234, 236, 238, 240 may be implemented in hardware as part of the microcontroller 220, or as software/firmware instructions programmed into the device and executed on the microcontroller 220 during certain modes of operation. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power precision amplifiers with programmable gain and/or automatic gain control, bandpass filtering, and a threshold detection circuit to selectively sense the cardiac signal of interest. The automatic gain control enables the exemplary device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 220 over signal lines 248 and 250 to control, for example, the gain and/or threshold of polarization charge removal circuitry (not shown) and the timing of blocking circuitry (not shown) optionally coupled to the inputs of the sensing circuits 244, 246.

Cardiac signals are supplied to an analog-to-digital (A/D) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

The microcontroller 220 is further coupled to a memory 260 by a suitable data/address bus 262. The programmable operating parameters used by the microcontroller 220 are stored in memory 260 and used to customize the operation of the exemplary device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the exemplary device 100 may be non-invasively programmed into the memory 260 through a telemetry circuit 264 in telemetric communication via communication link 266 with the external device 254, such as a programmer, local transceiver, or a diagnostic system analyzer. The microcontroller 220 can activate the telemetry circuit 264 with a control signal 268. The telemetry circuit 264 allows intracardiac electrograms and status information relating to the operation of the exemplary device 100 (as contained in the microcontroller 220 or memory 260) to be sent to the external device 254 through an established communication link 266.

The exemplary device 100 can further include one or more physiological sensors 270, for example "rate-responsive" sensors that adjust pacing stimulation rates according to the exercise state of the patient. Accordingly, the microcontroller 220 responds by adjusting the various pacing parameters (such as rate, AV Delay, V-V Delay, etc.) at which the atrial and ventricular pulse generators 222 and 224 generate stimulation pulses.

The physiological sensors 270 may further include sensors to detect bodily movement, changes in cardiac output, changes in the physiological condition of the heart, diurnal changes in activity (e.g., detecting sleep and wake states), G-force acceleration of the pacemaker case 200, length of the cardiac QT interval, blood oxygen saturation, blood pH, changes in blood pressure, changes in temperature, respiration rate, and QRS wave duration. While shown as being included within the exemplary device 100, the physiological sensor(s) 270 may also be external to the exemplary device 100, yet still be implanted within or carried by the patient.

Illustrated physiological sensors 270 include an activity/position sensor 271 (e.g., 3D accelerometer, movement sensor, etc.) to detect changes in the patient's position. A minute ventilation (MV) sensor 272 monitors breathing. Minute ventilation can be measured as the total volume of air that moves in and out of a patient's lungs in a minute. The MV sensor 272 may use transthoracic impedance, which is a measure of impedance across the chest cavity, from an impedance measuring circuit 278 to sense air movement. Lungs filled with air have higher impedance than empty lungs. Thus, upon inhalation, impedance increases and upon exhalation, impedance decreases.

Other illustrated physiological sensors 270 include a ventilatory cycle sensor 274 to track ventilatory cycles by alternative techniques other than thoracic impedance. The ventilatory cycle sensor 274 may use input from the ventilatory cycle probe 142. Signals generated by the physiological sensors 270 can be passed to the microcontroller 220 for use by the ventilatory histogram engine 240. Such signals can be used to detect and quantify apnea and invoke a responsive therapy.

The exemplary device 100 additionally includes a battery 276 that provides operating power to all of the components shown in FIG. 2. The battery 276 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 276 also desirably has predictable discharge characteristics so that elective replacement time can be detected. As one example, the exemplary device 100 employs lithium/silver vanadium oxide batteries.

The exemplary device 100 can further include magnet detection circuitry (not shown), coupled to the microcontroller 220, to detect when a magnet is placed over the exemplary device 100. A magnet may be used by a clinician to perform various test functions of the exemplary device 100 and/or to signal the microcontroller 220 that an external programmer (e.g., 254) is in place to receive or transmit data to the microcontroller 220 through the telemetry circuits 264.

The exemplary device 100 further includes the aforementioned impedance measuring circuit 278 that is enabled by the microcontroller 220 via a control signal 280. The impedance measuring circuit 278 can also be used for many things other than ventilatory cycle sensing, including: lead impedance surveillance during acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 278 may be coupled to the switch 226 so that any desired electrode may be used.

The exemplary device 100 may be operated as an implantable cardioverter/defibrillator device, which detects the occurrence of an arrhythmia and automatically applies an appropriate electrical shock therapy to the heart aimed at terminating the detected arrhythmia. To this end, the microcontroller 220 further controls a shocking circuit 282 via a control signal 284. The shocking circuit 282 generates shocking pulses of low (e.g., up to 0.5 joules), moderate (e.g., 0.5-10 joules), or high energy (e.g., 11 to 40 joules), as selected by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the case 200 may act as an active electrode in combination with the RV coil electrode 132, or as part of a split electrical vector using the SVC coil electrode 134 or the left atrial coil electrode 126 (i.e., using the RV coil electrode as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 220 is capable of controlling the synchronous or asynchronous delivery of the shocking pulses.

The exemplary device 100 can be programmed to treat both heart failure and sleep apnea. To treat heart failure, the device typically delivers pacing pulses of a voltage level via a lead in the left-sided veins. More generally, the exemplary device 100 can be programmed to stimulate different sets of muscles through the same lead/electrode system. The exemplary device 100 can be programmed to vary the output voltage of various pulses to effectively stimulate different muscles of the heart, even though the lead and electrode placement does not change.

Exemplary Ventilatory Histogram Engine

Figure 3:
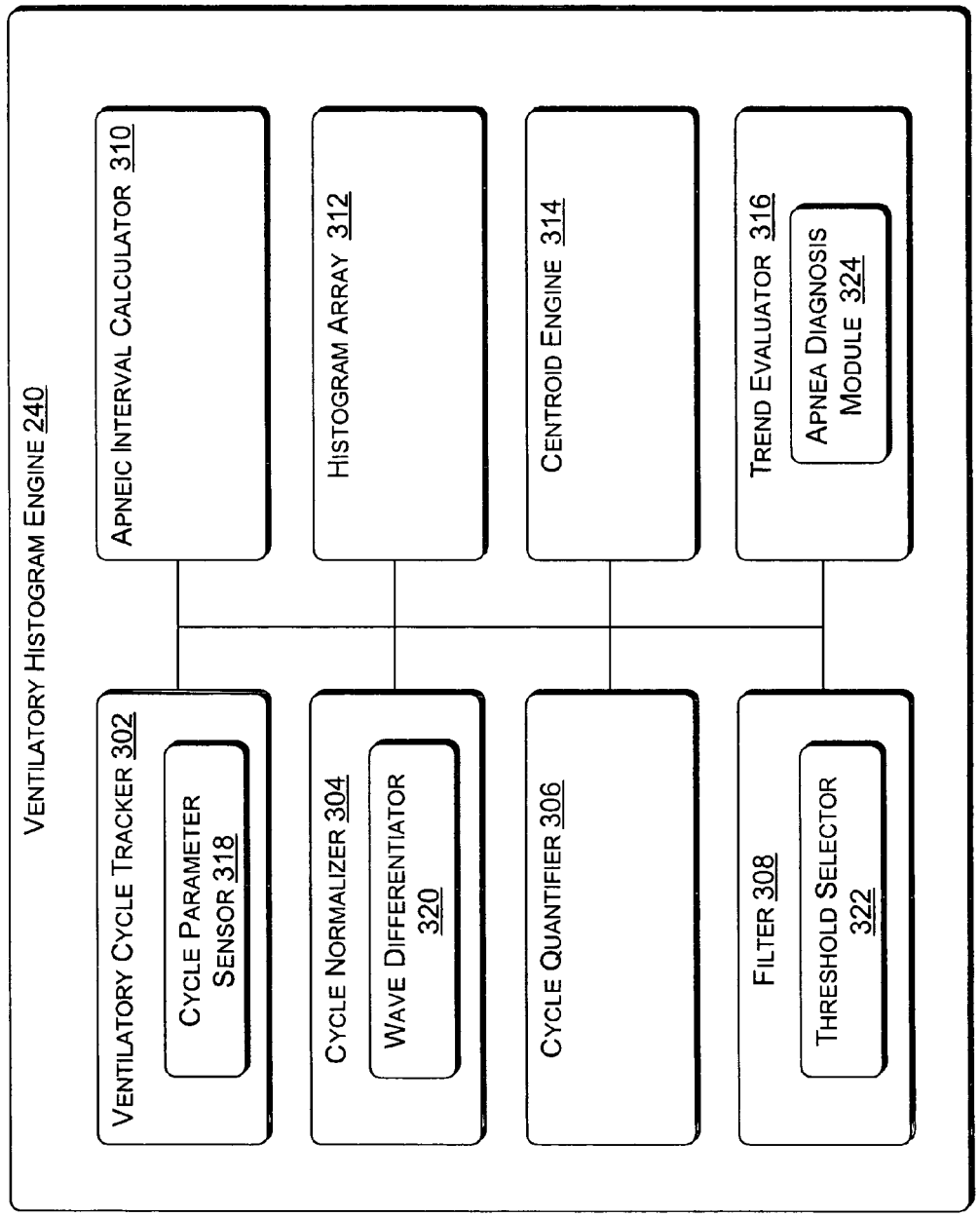
FIG. 3 is a block diagram of the ventilatory histogram engine of FIG. 2 in greater detail.

FIG. 3 shows the exemplary ventilatory histogram engine 240 of FIG. 2 in more detail. A ventilatory histogram engine 240 can maintain a real-time or near real-time histogram of breathing and apnea activity. The ventilatory histogram engine 240 includes a ventilatory cycle tracker 302, cycle normalizer 304, a cycle quantifier 306, filter 308, apneic interval calculator 310, real-time histogram array 312, centroid engine 314, and trend evaluator 316. These components can be communicatively coupled, with one exemplary coupling being illustrated in FIG. 3.

The ventilatory cycle tracker 302 may further include a cycle parameter sensor 318, the cycle normalizer 304 may further include a wave differentiator 320, the filter 308 may further include a threshold selector 322, and the trend evaluator 316 may further include an apnea diagnosis module 324. It should be noted that an exemplary ventilatory histogram engine 240 can be hardware, software, firmware, etc., or a combination thereof.

The ventilatory cycle tracker 302 senses and records cycles of inspiration and expiration or at least derives a parameter related to ventilation that can be used to track ventilation cycles. Thoracic impedance can be used to track ventilation cycles as thoracic impedance is proportional to tidal volume, but a cycle parameter sensor 318 can include other sensors and/or probes that can be used instead of or in addition to thoracic impedance, such as a mechanical movement sensor, an optical sensor of lung movement, a pneumatic pressure sensor, a blood chemistry sensor, etc. Example functions performable by a ventilatory cycle tracker 302 are described more fully below with respect to FIG. 5.

The cycle normalizer 304 aims to relate each breathing cycle to the same frame of reference. In other words, the cycle normalizer 304 "levels the playing field" if cycle data gathered from the patient includes drift artifacts. A wave differentiator 320 may be used to produce a purer ventilation cycle waveform by removing other superimposed drift waveforms. Example functions performable by a cycle normalizer 304 are described more fully below with respect to FIG. 6.

A cycle quantifier 306 derives or assigns a quantity or magnitude to each of multiple ventilation cycles for purposes of comparing and filtering. Example functions performable by a cycle quantifier 306 are described more fully below with respect to FIGS. 7-8.

The filter 308 separates sensed cycles based on the quantities assigned by the cycle quantifier 306. A threshold selector 322 may be used to determine criteria for separating normal ventilation cycles from apneic ventilation cycles.

Example functions performable by a filter 308 are described more fully below with respect to FIG. 9.

The apneic interval calculator 310 measures or derives time intervals representing the durations of apnea episodes. Example functions performable by an apneic interval calculator 310 are described more fully below with respect to FIG. 9.

The histogram array 312 stores apneic interval information obtained from the apneic interval calculator 310 and is capable of being updated in real-time or near real-time with incoming ventilation cycle data gathered from a patient. Exemplary histograms storable in a real-time histogram array 312 are described more fully below with respect to FIGS. 10-11.

The centroid engine 314 capsulizes clusters of the apneic interval information into centroids. Thus, the centroids are summaries of the apneic interval information that require very little storage space. Example functions of a centroid engine are further described below with respect to FIGS. 11-12.

The trend evaluator 316 recognizes changes and/or movement in the centroids of a ventilatory histogram that may signal a trend change in the patient's health. This is discussed further with respect to FIG. 12. The apnea diagnosis module 324 decides if apnea is present, based on a threshold or standard.

Other devices and engines may also practice the exemplary methods described herein. The illustrated ventilatory histogram engine 240 is just one example of a hardware and/or software mechanism for practicing the subject matter.

Exemplary Methods

Figure 4:
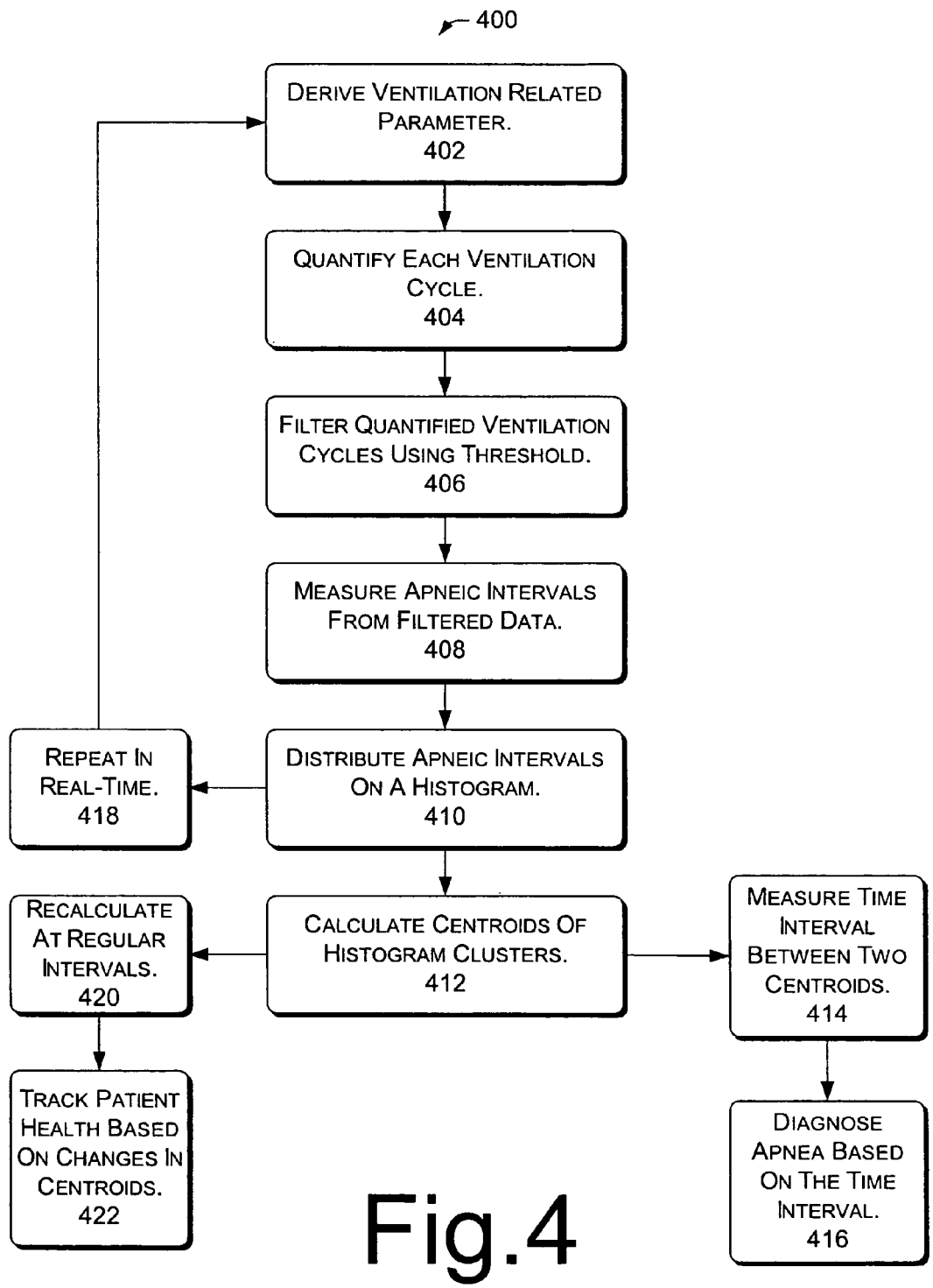
FIG. 4 is a flow diagram of an exemplary real-time method for detecting and quantifying apnea.

FIG. 4 shows an exemplary method 400 for detecting and quantifying apnea that may be practiced in real time. This exemplary method 400 may be performed by an implantable device, such as the exemplary device 100, which can be programmed to detect and quantify apnea as well as apply cardiac pacing pulses to treat a heart condition, or by an exemplary ventilatory histogram engine 240.

In the flow diagram, the operations are summarized in individual blocks. The operations may be performed in hardware and/or as machine-readable instructions (software or firmware) that can be executed by a device, such as an exemplary device 100, which includes a microcontroller 220 and/or a ventilatory histogram engine 240.

At block 402, a ventilation related parameter is derived in real-time, for example, by a ventilatory cycle tracker 302 and in some variations, by a cycle normalizer 304. The ventilation related parameter is capable of tracking the depth, tidal volume, and/or timing of a patient's respiratory inspirations and expirations, i.e., the patient's ventilatory cycles. Thoracic impedance, that is, variations in thoracic impedance over time, is one example of a ventilation-related parameter that can be used, as will be described with respect to FIGS. 5-6. Other parameters could also be used instead of thoracic impedance, as long as a selected parameter reflects the cycling of a patient's breathing, which can be used to diagnose apnea.

At block 404, ventilatory cycles are quantified, for example, by a cycle quantifier 306 of an exemplary ventilatory histogram engine 240. In one implementation, relative magnitudes of inspiration are derived by calculating the rate of change of thoracic impedance with respect to time at regular intervals, for example, every second, or every fraction of a second. The rate of change values are combined into a single value for each inspiration and expiration. Thus, successive "valley-to-peak" expiration and inspiration values are determined in real-time to quantify each ventilatory cycle and successive single values representative of each ventilatory cycle can be compared to determine presence of apnea.

At block 406, quantified ventilation cycle values (such as valley-to-peak values) for apneic breathing are filtered from values for normal breathing using a selected threshold, for example, by a filter 308 that may include a threshold selector 322. Ventilation cycle quantification is facilitated by the bimodality of normal ventilation data versus apneic ventilation data, as illustrated in FIG. 9. A marked polarization in the data often results in a relatively easy separation of the two. Most of the normal breathing values are relatively high and most of the apnea breathing values are relatively low. This leaves a gap in the cycle values as shown in FIG. 9 that can be approximated with many types of threshold values, such as a simple moving average of the instantaneously measured ventilation cycle values.

At block 408, apneic intervals between at least some of the valley-to-peak values for normal breathing are measured in real-time, for example, by an apneic interval calculator 310. As shown in FIG. 9, once the normal breathing cycle values and the apneic breathing cycle values are demarcated from each other, determining the time interval between the end of one period of normal breathing and the beginning of the next can be a mere single measurement along a time axis. To measure apneic intervals in real-time can be accomplished by beginning a count once a ventilatory cycle tracker 302 senses a ventilation cycle value that exceeds the threshold. In one variation, if an additional ventilation cycle value does not exceed the threshold within a certain time period, then the first ventilation cycle that exceeded the threshold is disregarded as a false indicator of a period of normal breathing. But in another variation, a single deep breath is regarded as a period of normal breathing in itself.

At block 410, the apneic intervals are distributed as counts on a histogram, for example, in a histogram array 312 of an exemplary ventilatory histogram engine 240. As shown in FIG. 10, the most frequently occurring apneic intervals receive the highest count on a histogram. Hence, brief normal pauses in breathing of approximately ten seconds may register as the highest count. The counts of truly apneic intervals have a tendency to form a frequency distribution curve clustered in one part of a histogram. This frequency distribution can contain a great deal of information about the patient's apnea.

At block 412, centroids are calculated for clusters of the apneic intervals distributed as counts on the histogram, for example, by a centroid engine 314. As shown in FIG. 11, calculating intermediate centroids for simple shapes that constitute or approximate a more complexly shaped cluster or distribution curve may expedite calculation of an overall centroid for the curve or cluster. Overall centroids representing either cumulative periods of apnea or cumulative pauses in periods of normal breathing can summarize much information using just a few histogram coordinate values to describe each centroid.

At block 414, a time interval is measured between two of the centroids, for example, by a centroid engine 314 and/or a trend evaluator 316. As shown in FIG. 11, the time interval between overall centroids has value for tracking some patient health trends. Relatively long term changes in the time interval, as shown in FIG. 12, can demonstrate that a patient's respiratory and/or cardiac condition is changing.

At block 416, an apnea diagnosis is based on the time interval between overall centroids, for example, by an apnea diagnosis module 324 programmed to discern apnea from non-apnea. The programming might include an accepted threshold for apnea or even a more complex algorithm that examines multiple aspects of the centroids and the patient's breathing to arrive at a diagnosis.

At block 418, centroids are recalculated at regular intervals. For example, an exemplary ventilatory histogram engine 240 may recalculate centroids based on an hour's, a day's, a week's worth, etc. of new ventilatory cycle data. Shorter recalculation times may be more useful in acute or new patients, while longer recalculation times may be suitable for long term preventative maintenance and trend tracking.

At block 420, patient health is tracked based on changes in the centroids. Daily centroids or longer term changes in relationships between centroids may be stored in an exemplary device 100 or exported to an external device 254. The stored data can be used for many levels of patient health analysis.

Figure 5:
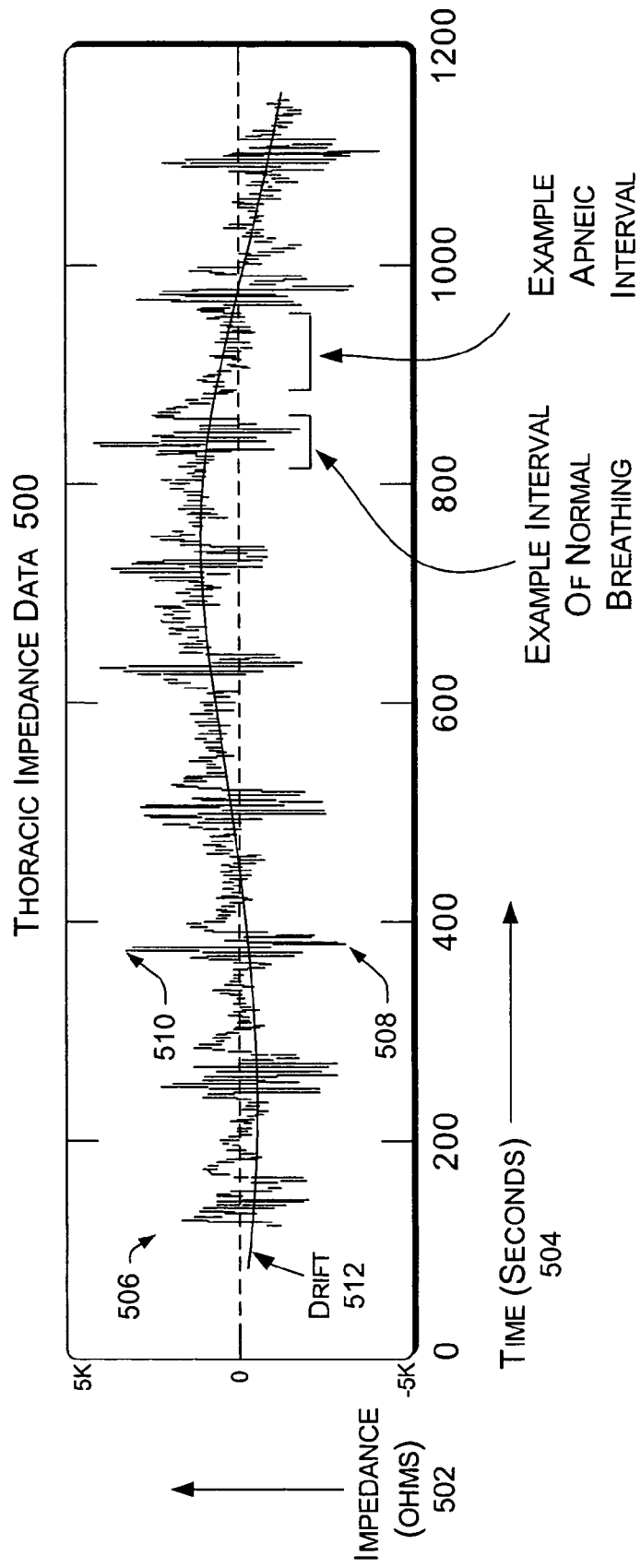
FIG. 5 is a graphical representation of exemplary thoracic impedance data used as a ventilation related parameter in an exemplary method.

FIG. 5 shows real-time measurement of thoracic impedance data 500. Measuring thoracic impedance 502 against time 504 constitutes one part of an exemplary method for detecting and quantifying apnea that may be performed by a ventilation cycle tracker 302 of an exemplary ventilatory histogram engine 240.

Thoracic impedance data 500 gathered in real-time by an exemplary method can be thought of as a virtual real-time pneumograph of a patient's ventilation. In one implementation, the thoracic impedance data 500 is measured as lowpass filtered impedance (Z) in ohms versus time 504 in seconds.

Described in greater detail, the subject matter detects a patient's ventilatory cycle waveform by measuring impedance variations 506 over time through a partial cross section of chest. These thoracic impedance variations 506 can be measured by injecting a constant current (e.g., an alternating current (AC) of frequency 50-500 kHz) between electrodes of an implantable device. Several different electrodes can be used, for example from a case 200 to a right ventricular tip electrode 128, from a case 200 to a right atrial ring electrode 121, from a case 200 to a right atrial tip electrode 120, from a case 200 to a right ventricular coil electrode 132, etc.

The AC current travels transthoracic electrical paths, including through the lungs. As a patient breathes, changes in air volume in the alveoli of the lungs cause a corresponding net change in impedance between the electrodes. Fixed resistors of high value can be connected in series with each electrode to enable the constant current source. The changing voltage applied across the resistors to maintain the constant current during conditions of changing impedance represents the breathing pattern or ventilatory cycle of the patient. The changes in breathing and associated impedance variations 506 measured, for example, as voltage variations over time, provide an electrical analogy of the ventilatory valleys 508 and peaks 510 of a conventional respiratory spirogram. The lowpass filtering feature may be optionally included to remove residual signals, such as carrier signal artifacts.

The exemplary thoracic impedance data 500 may include long waveform variations referred to herein as "drift" 512 during measurements of the impedance variations 506 characteristic of short waveform patient breathing. The relative valley-to-peak magnitudes for inspiration and expiration in a given respiratory state remain the same despite the drift 512, however, so the long waveform drift 512 can be removed to yield a purer waveform of the patient's ventilatory cycling. Drift 512 in the ongoing impedance measurements (or voltage measurements if voltage is used to measure the impedance) may be caused by subtle changes in transthoracic electrical paths, e.g., may be caused by changes in lung volume from factors unrelated to the patient's ventilatory cycle, such as minute electrical path ionizations, changes in physical circuitry characteristics of an implantable device, changes in battery charge, changes in body position, changes in lung geometry due to body fluid balance or a nearby organ, a full stomach, etc. Regardless of its cause, the drift 512 can be eliminated by one of several techniques.

Figure 6:
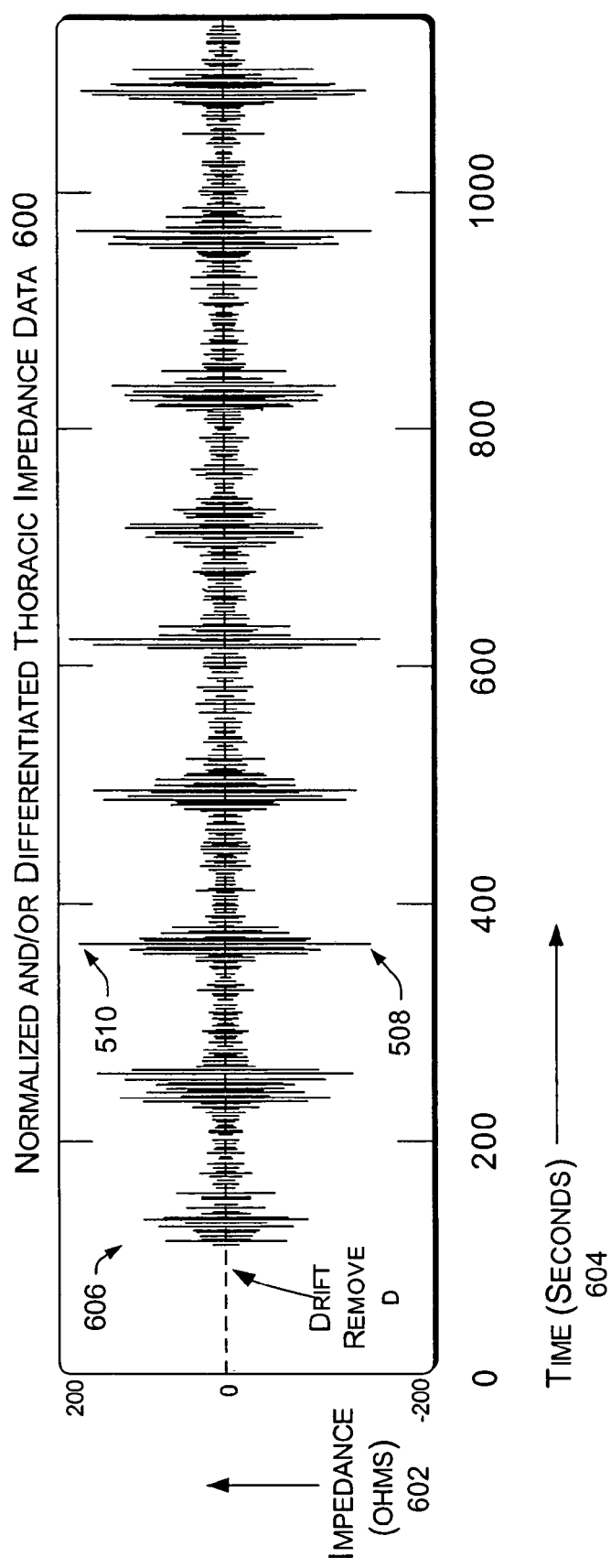
FIG. 6 is a graphical representation of exemplary normalized thoracic impedance data.

FIG. 6 shows normalized impedance data 600 that may be obtained by a cycle normalizer 304 of an exemplary ventilatory histogram engine 240. In one implementation, the impedance variations 506 over time that correspond to a patient's breathing cycles—or lack thereof during apnea—are simultaneously or subsequently normalized to remove the drift 512, if any. In another implementation, a derivative of the ongoing thoracic impedance measurements (or measurements of another ventilatory parameter), for example, rate of change of the thoracic impedance, is approximated and/or calculated in real-time or near real-time and normalization of data occurs automatically by virtue of the derivative approximation. If the derivative function is rate of change of thoracic impedance, then the endpoints of inspiration and expiration—defined by no change in thoracic impedance—automatically scale to a zero line regardless of absolute thoracic impedance being measured.

If some other method of quantifying the magnitude of ventilatory cycles is being used besides rate of change of thoracic impedance, then data may be calibrated to a zero line to remove drift 512. Such an exemplary normalization method aims to eliminate all waveforms not related to the patient's ventilatory cycle. For example, since drift 512 can be considered a raised or lowered moving average of the instantaneously measured ventilatory parameter, elimination of drift 512 can be accomplished, in one implementation, by subtracting an ongoing moving average (e.g., a twenty minute moving average) of the measurements from each instantaneous measurement (i.e., in the case of impedance, if the moving average is positive then the subtraction lowers the moving average back down to a y=0 value on the axis of thoracic impedance 502 and if the moving average is negative the subtraction operation raises the moving average back up to the y=0 value on the axis of thoracic impedance 502).

It should be reiterated that thoracic impedance variations 506 may be measured by voltage variations or other electrical quantities, in which case the analogous voltage measurements or other measured quantities are normalized instead of the impedance variations 506.

Figure 7:
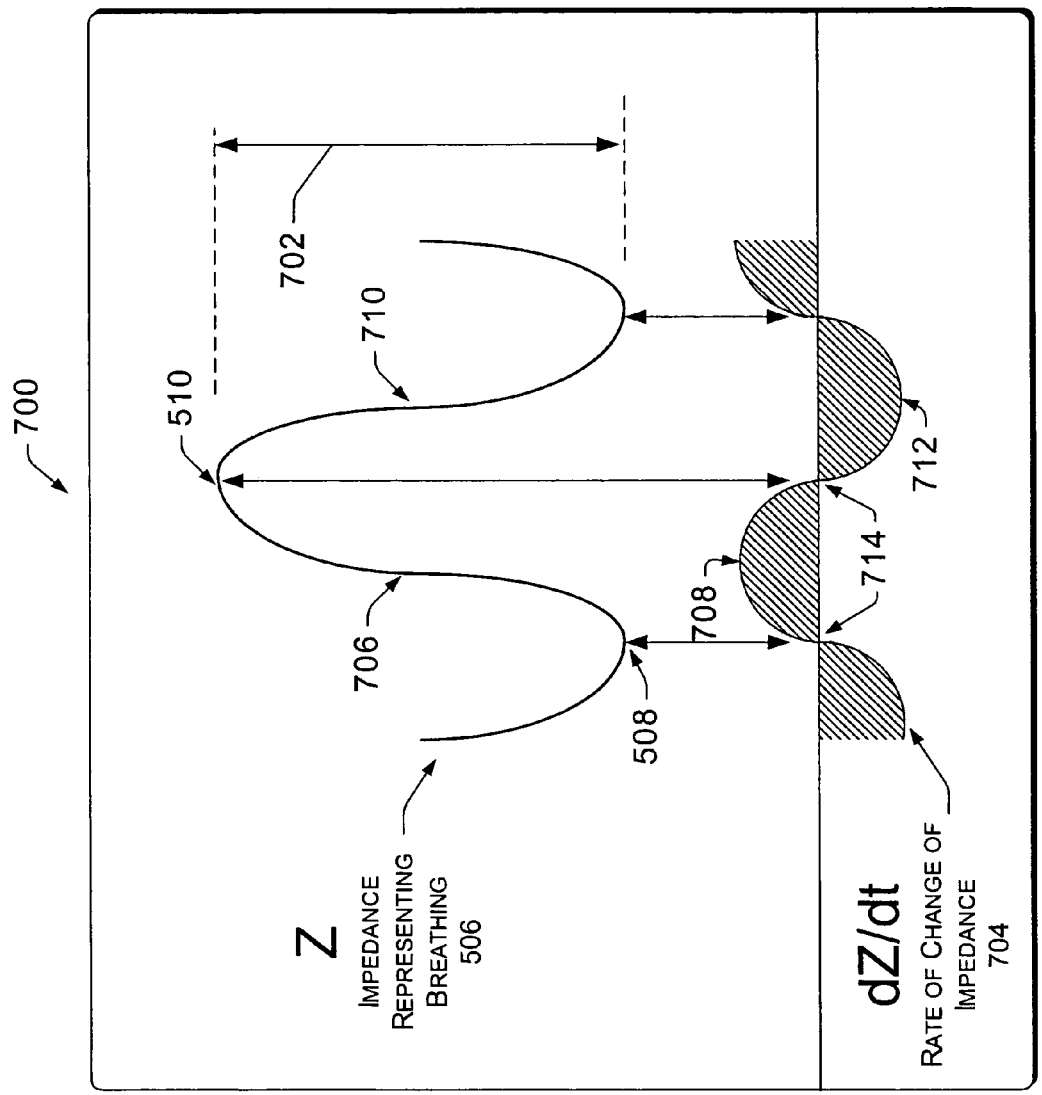
FIG. 7 is a graphical representation of an exemplary method of obtaining magnitude of ventilation values from a thoracic impedance rate of change derivation.

FIG. 7 shows a sample of valley-to-peak thoracic impedance data 700 in greater detail than in FIGS. 5 and 6. The valley-to-peak (or peak-to-valley) distance 702 represents tidal volume, the capacity of the lungs from a state of expiration to a state of inspiration within a single ventilation cycle. Tidal volumes are relatively small during apnea/hypopnea and relatively large during normal ventilation.

Raw thoracic impedance measurements 506 that represent inspiration and expiration can be measured directly by an exemplary IED 100 but the measurements may need to be subjected to interpretation in order to decide when apnea is occurring. In one implementation, rather than thoracic impedance "Z" itself, a derivative function of thoracic impedance that lends itself to diagnosis of apnea is either derived or approximated by calculation. One such derivative of impedance is the rate of change of the impedance with respect to time 704. In the middle of inspiration 706, the lungs are filling at the fastest rate of the entire ventilatory cycle and the rate of change of the measured impedance is greatest in a positive direction 708. During the middle of expiration 710, the lungs are emptying at the fastest rate of the entire ventilatory cycle and the rate of change of the impedance is greatest in a negative direction 712. At the valleys 508 and peaks 510 of the ventilatory cycle, when the lungs are empty or full, there is not much volume change in the lungs and consequently the rate of change of the impedance becomes zero momentarily 714.

In one implementation, the above-described rate of change derivative is employed to diagnose and monitor apnea/hypopnea because exemplary methods to calculate an approximation of the rate of change of impedance in real-time use very little energy and may also use preexisting data—i.e., thoracic impedance measurements 506, which are typically already being gathered by an exemplary IED 100 for various other purposes.

Figure 8:
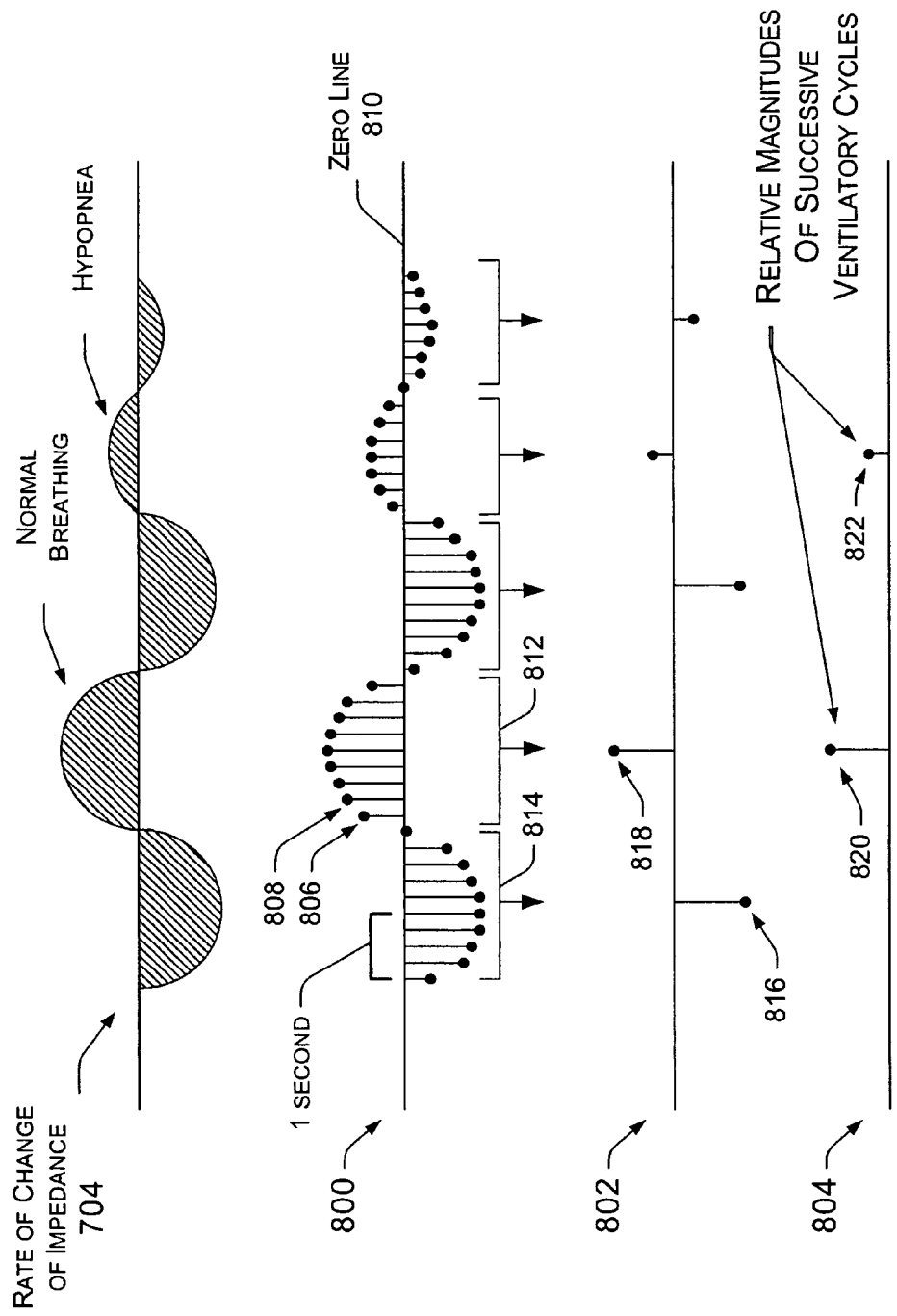
FIG. 8 is a graphical representation of an exemplary method of calculating magnitude of ventilation values from thoracic impedance rate of change approximations.

FIG. 8 shows first segments (800, 802, 804) of an exemplary method for detecting and quantifying apnea. A plot of the rate of change derivative 704 depicts normal breathing that lapses into hypopnea over an interval of two-and-a-half ventilatory cycles.

In one implementation a device, such as an exemplary IED 100 that includes a wave differentiator 320 and/or a cycle quantifier 306 of an exemplary ventilatory histogram engine 240, approximates the rate of change of thoracic impedance 704 by calculations performed at regular intervals, shown in another rate of change plot 800. A patient at rest has a breathing rate of approximately twelve to twenty breaths per minute. At twelve breaths per minute one breath occurs about every five seconds. If the device or engine is arbitrarily set to perform a rate of change (of thoracic impedance) approximation every quarter second, then each ventilatory cycle—one inspiration and one expiration—can be described by approximately twenty rate of change values as shown in the rate of change plot 800.

In one implementation, an exemplary technique for performing each impedance rate of change calculation (e.g., 806; 808) consists of subtracting the most recent past thoracic impedance measurement from the current thoracic impedance measurement (i.e., referring to 506 of FIG. 7, the current thoracic impedance "$Z_{current}$" during the current rate of change calculation 808 minus a thoracic impedance "$Z_{previous}$" at the time the previous rate of change calculation 806 was performed) according to Equation (1):

$$\Delta Z = Z_{current} - Z_{previous} \qquad (1)$$

Thus, each data point (e.g., 806; 808) on the rate of change plot 800 represents one performance of Equation (1). During inspiration, thoracic impedance is increasing, successive current thoracic impedance values are greater than previous thoracic impedance values, and Equation (1) yields positive values. During expiration, thoracic impedance is decreasing, successive current thoracic impedance values are less than previous thoracic impedance values, and Equation (1) yields negative values. At the completion of inspiration or the completion of expiration there is little or no change in thoracic impedance and Equation (1) yields values for the pause between inspiration and expiration (or vice versa) on or near the zero line 810.

Using the zero line 810 to distinguish groups of positive values (e.g., 818) of Equation (1) obtained during inspiration from groups of negative values (e.g., 816) of Equation (1) obtained during expiration, each group of positive values 818 represents a valley-to-peak distance 702 of ventilation as shown in FIG. 7, while each group of negative values 816 represents the reverse, a peak-to-valley distance (702). Each group of positive or negative $\Delta Z$ solutions of Equation (1) (i.e., each valley-to-peak distance, peak-to-valley distance, half ventilatory cycle, etc.) can be summarized by a single centroidal data point (e.g., 816; 818). A plot of summarized inspirations and expirations 802 over time shows one data point (e.g., 818) for each inspiration and one data point (e.g., 816) for each expiration. Each summary data point "$\Delta z_{summary}$" can be the centroid, average, mean, etc., of the multiple $\Delta Z$ data points in a respective group (e.g., 814).

Since depth of inspiration and depth of expiration in any given ventilatory cycle tend to be symmetrical, that is, the depth of expiration tends to equal the depth of inspiration regardless of whether a patient has normal breathing, hypopneic breathing, or apneic breathing, either the inspirations or the expirations may be used to detect and quantify dyspneic breathing. Combined inspirations and expirations as shown in 802 are not needed. Hence, a half-wave rectification of inspiration and expiration data points (as in 802) yields a plot of inspirations 804 (or alternatively, expirations) consisting of one $\Delta z_{summary}$ data point for each inspiration. Since each data point is a summary of an entire inspiration, multiple data points representing successive inspirations over time can be used to gauge changes in relative magnitudes of ventilation.

Over a selected timeframe an apneic patient's breathing is bimodal, allowing the inspiration data points as in 804 recorded during the timeframe to be resolved into two sizes: relatively large $\Delta z_{summary}$ values 820 for periods of normal breathing and relatively small $\Delta z_{summary}$ values 822 for periods of apnea. In other words, a series of abnormally small inspiration data points intervening between two large normal inspiration data points can be taken as an apneic interval.

Figure 9:
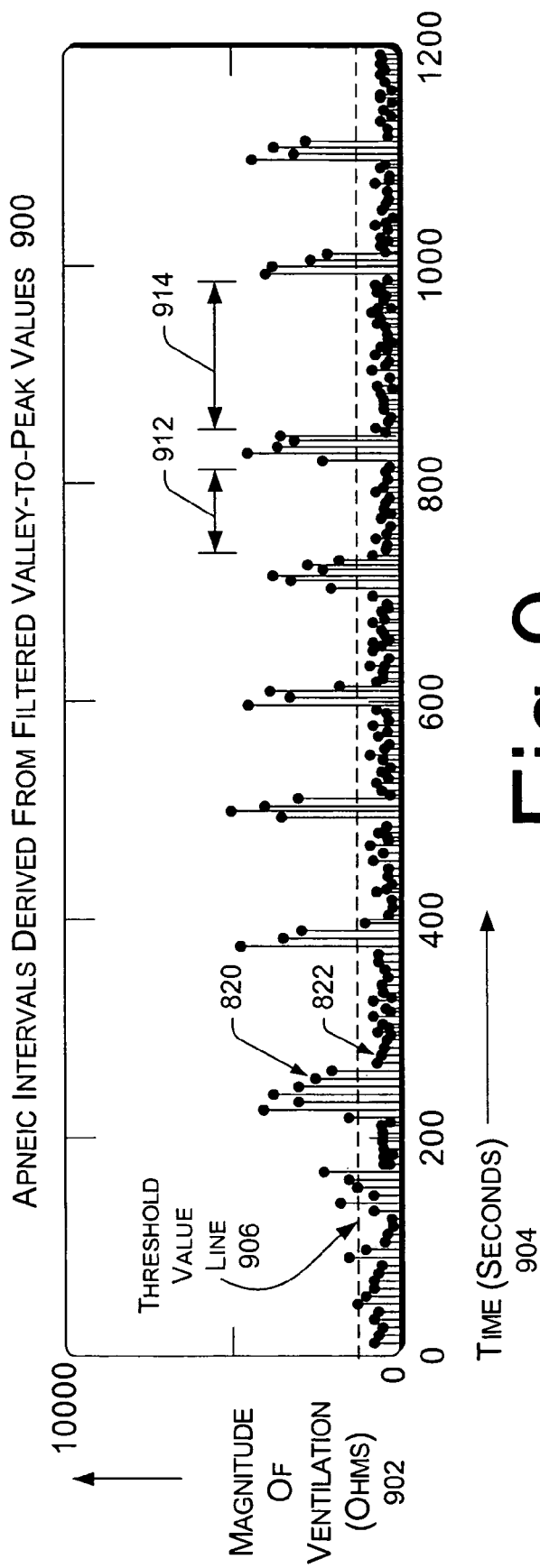
FIG. 9 is a graphical representation of an exemplary method for determining apneic intervals from filtered magnitude of ventilation values.

FIG. 9 shows apneic interval derivation 900 from filtered $\Delta z_{summary}$ values for successive inspirations. FIG. 9 thereby illustrates an exemplary technique for filtering bimodal $\Delta z_{summary}$ values based on a threshold and determining apneic intervals from the filtered values. The exemplary technique may be performed by an apneic interval calculator 310 of an exemplary ventilatory histogram engine 240.

A collection of successive $\Delta z_{summary}$ values representing magnitudes of ventilation 902 can be plotted with respect to a time axis 904. In one implementation, each $\Delta z_{summary}$ value may be stored in memory or in a data file and associated with a time value. After multiple $\Delta z_{summary}$ values are obtained, e.g., twenty minutes worth of patient breathing, a threshold value 906 can be determined for filtering or "binarizing" the $\Delta z_{summary}$ values in order to separate values associated with normal breathing (e.g., 820) from values associated with apnea (e.g., 822). Since the majority of the values are polarized into either a normal breathing value range or into an apneic breathing value range, using a most frequently occurring value for demarcating the two bimodal ranges, as is commonly practiced in some forms of image binarizing, generally does not work. But other thresholding metrics work well, such as standard deviation curves; mean moving averages of all $\Delta z_{summary}$ values; standard deviations from a mean multiplied by a factor; etc. Alternatively, a threshold based on a medical definition of apnea can be used. For example, a definition stating that ventilation with a tidal volume of less than "X" percent of a patient's normal tidal volume over a certain period of time is considered apneic can be used as the filtering threshold after calculating a patient's normal average tidal volume.

Once a threshold value 906 for separating normal (e.g., 820) from apneic (e.g., 822) $\Delta z_{summary}$ values is selected, then in one implementation the apneic values 822 are filtered out, or at least temporarily ignored. Apneic intervals, e.g., 912, 914, between the remaining values that represent normal breathing can now be measured or computed. Each apneic interval (912 or 914) represents a time duration of an individual episode of apnea. The term "apneic interval" will also be used herein to described brief breathing pauses that are not always strictly apneic, in other words, an apneic interval for calculation purposes here can be any pause in normal, continuously cycling ventilation.

Each time an apneic interval is measured or computed, whether after the end of a selected timeframe or in an ongoing, real-time manner, the particular apneic interval value obtained is used to increment an exemplary histogram.

FIG. 10 shows an exemplary histogram 1000 that plots a count of apnea episodes 1002 with respect to the durations or "apneic intervals" 1004 of the counted apnea episodes 1002. In other words, an exemplary histogram 1000 portrays a distribution of the various durations of a patient's apnea episodes along a timeline. A histogram array 312 of an exemplary ventilatory histogram engine 240 may store the exemplary histogram 1000.

Histogram bin "A" 1006 and histogram bin "B" 1008 comprise a first "cluster" 1010 of counted episodes that have similar apneic intervals. Bin A 1006, for example, shows a count of fifty episodes of "apnea" in which normal breathing stopped or was significantly reduced—below the selected threshold value 906—for 0-10 seconds. Bin B 1008 shows five episodes in which normal breathing stopped or was significantly reduced for 10-20 seconds. These 0-20 second breathing pauses in the first cluster 1010 consisting of Bin A 1006 and Bin B 1008 are not long enough to be considered apneic. However, the first cluster 1010 of "normal" brief apneic intervals provides a frame of reference for comparing a second cluster 1012 of apnea episodes in which the durations of the breathing pauses are apneic, at least with respect to the selected threshold value 906.

Bins C, D, E, F, and G (1014, 1016, 1018, 1020, and 1022) represent the aforementioned second cluster 1012 comprising apnea episodes that have apneic intervals (i.e., durations) of between 70-120 seconds. These bins are referred to as a second cluster 1012 because they are adjacent in time and because no intervening apnea episodes that have apneic intervals between 20-70 seconds are counted between the first cluster 1010 and the second cluster 1012 to obscure separation of the two clusters.

Bins E 1018 and F 1020, which have the highest episode counts, reveal that most of the patient's apnea episodes are between 90-110 seconds long. Frequency of occurrence for other apneic intervals can also be gauged by the exemplary histogram 1000. However, in the illustrated second cluster 1012, only approximately seventeen episodes of apnea have been counted. A real life exemplary histogram 1000 might record several hundred apnea episodes per night, and correspondingly might reveal a more complex distribution of apnea episodes than the illustrated example.

An exemplary histogram 1000 is stored for ongoing updating as thoracic impedance data 500 is collected from a patient. In other words, episode counts (1002) for each histogram bin are stored in an array or file that can be incremented in real-time. In one implementation, an exemplary histogram 1000 undergoes various data processing techniques, such as cluster analysis, once per day. One cluster analysis technique that can be performed and/or updated daily includes computation of cluster centroids.

A clustering algorithm that represents each cluster by a centroid derived from cluster bin members can be used, e.g., by a centroid engine 314 of an exemplary ventilatory histogram engine 240, to compute one or more centroids for an exemplary histogram 1000. Techniques for calculating centroids may each have inherent advantages and disadvantages. For example, techniques that use averaging of cluster members may be thrown off by members that only marginally belong to the cluster, such as aberrant members that may be overly represented if they really belong to a different cluster. Techniques that use a single representative member from a cluster as the centroid may suffer if the representative member has attributes not shared by the other members. In an exemplary histogram 1000, there may be too few members in a cluster to use a representative member technique, but the representative member technique and its potential usefulness for an exemplary histogram 1000 is noted.

One exemplary technique for determining centroids uses a center of mass approach, treating a cluster (e.g., 1012) on an exemplary histogram 1000 or an individual bin member in the cluster as if it were a plane shape of uniform density. The centroid of a plane shape is that point about which the total moment of the system is zero. In symmetrical plane shapes the points and lines on the plane shape where the total moment is zero are always on some axis of symmetry. Thus, computational power in an exemplary device 100 can be conserved by calculating centroids for each symmetrically shaped bin rectangle in an exemplary histogram cluster 1012. These are later combined, rather than trying to perform only one, more computationally intensive calculation on the entire irregular cluster 1012, such as approximating an integral, numerical integration, etc. Hence, in one implementation, centroids are calculated for simple rectangular bin shapes, and then the centroids are weighted according to the relative size of their respective bins and averaged to obtain an overall centroid that represents the entire cluster 1012. This will be described next. Of course, many other techniques for computing histogram cluster centroids may be used with the subject matter.

FIG. 11 shows an exemplary histogram 1100 similar to that shown in FIG. 10. For each of the two clusters 1010, 1012, centroids are calculated for each bin in a cluster (the dark dots). Thus separate centroids are determined for each of bins A-G. The centroids are then weighted according to their respective bin count and averaged to obtain an overall centroid for each cluster.

In the first cluster 1010, the centroid 1102 for bin A 1006 is at the (x, y) coordinate pair (5, 25). These values for the ordered pair are simply those coordinates of the center point along two midlines of each respective dimension of the rectangular bin A 1006. Likewise, the same determination results in a centroid 1104 for bin B 1008 at coordinates (15, 2.5). Now the two bin centroids are combined. Bin A 1006 receives 50/55 of the weight in the averaging calculation while bin B 1008 receives 5/55 of the weight, due to their respective magnitudes.

The x and y coordinates for the overall centroid 1106 for the first cluster 1010 can be calculated as shown in Equations (2) and (3):

$$W_1(x_1)+W_2(x_2)=x_O \quad (2)$$

$$W_1(y_1)+W_2(y_2)=y_O \quad (3)$$

where W equals the magnitude of a particular bin divided by the magnitude of all bins in a cluster, and $x_O$ and $y_O$ are the coordinates of the overall centroid a cluster. Accordingly, for the first cluster 1010, $x_O$ and $y_O$ are calculated as in Equations (4) and (5):

$$x_O=50/55(5)+5/55(15)=6 \quad (4)$$

$$y_O=50/55(25)+5/55(2.5)=23 \quad (5)$$

Thus, the overall centroid 1106 for the first cluster 1010 is located at approximately (6, 23) on the exemplary histogram 1100.

Likewise, an overall centroid 1108 for the second cluster 1012 may be calculated using centroids determined for each individual bin in the cluster 1012. Centroids for each bin are determined by finding center points along two midlines of each respective rectangular bin. Centroids are determined to be at (75, 0.5) for bin C 1014, at (85, 0.5) for bin D 1016, at (95, 2.5) for bin E 1018, at (105, 3.5) for bin F 1020, and at (115, 1.5) for bin G 1022. The episode count 1002 for all the combined bins of the second cluster 1012 equals 17. For weighting purposes, W equals 1/17 for bin C 1014, W equals 1/17 for bin D 1016, W equals 5/17 for bin E 1018, W equals 7/17 for bin F 1020, and W equals 3/17 for bin G 1022.

Equations (6) and (7) show calculations for finding the coordinates $x_O$ and $y_O$ of the overall centroid 1108 of the second cluster 1012 using instances of Equations (2) and (3):

$$x_O = 1/17(75) + 1/17(85) + 5/17(95) + 7/17(105) + 3/17(115) = 101 \quad (6)$$

$$y_O = 1/17(0.5) + 1/17(0.5) + 5/17(2.5) + 7/17(3.5) + 3/17(1.5) = 2.5 \quad (7)$$

Thus, the overall centroid 1108 for the second cluster 1012 is located at approximately (101, 2.5) on the exemplary histogram 1100.

FIG. 12 depicts a centroid movement plot 1200 for tracking patient health. An increase in the number of apnea episodes a patient experiences over multiple iterations of a timeframe results in centroid movement of an overall centroid 1108 for the second cluster 1012 along the episode count axis 1002 (y-axis). An increase in the average duration of apnea episodes a patient experiences over multiple iterations of a timeframe results in centroid movement of an overall centroid 1108 for the second cluster 1012 along the apneic interval axis 1004 (x-axis).

Returning to FIG. 11, an overall apneic interval 1110 between the two overall centroids 1106, 1108 can be measured or calculated. For example, a difference between the two x-axis coordinates of the two centroids 1106, 1108 can be calculated, as shown in Equation (8):

$$x_{O2} - x_{O1} = \text{overall apneic interval.} \quad (8)$$

An overall apneic interval of:

$$101 - 6 = 95 \text{ seconds} \quad (9)$$

is obtained. This overall apneic interval 1110 can be compared with a pre-selected value, such as a textbook threshold (e.g., 30 seconds), in order to perform an in vivo diagnosis of apnea by an exemplary device 100. In this case, the 95 second overall apneic interval 1110 is greater than a hypothetical 30 second threshold, resulting in a diagnosis of apnea. The determination of an overall apneic interval 1110 or, detection of changes in the overall apneic interval 1110 over time can be used to activate treatment and/or monitoring algorithms in an implantable device. The various centroids described above can be stored over months to track a patient and their storage uses only a sparing amount of memory.

CONCLUSION

The foregoing discussion describes methods for detecting and quantifying apnea using ventilatory cycle histograms. Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. A method comprising:
   deriving a ventilation related parameter in real-time from a patient;
   deriving apneic intervals from the parameter;
   distributing the apneic intervals as counts on a histogram;
   calculating a centroid for each cluster of counts on the histogram diagnosing apnea as a function of the centroids; and
   and delivering therapy to the patient in response to the detection of apnea.

2. The method as recited in claim 1, wherein deriving apneic intervals comprises:
   determining a value for each ventilation cycle based on the parameter;
   filtering the values using a threshold value to separate values representing normal ventilation cycles from values representing apneic ventilation cycles; and
   measuring the apneic intervals between the filtered values representing periods of normal ventilation.

3. The method as recited in claim 2, wherein the parameter comprises variations in thoracic impedance in response to breathing.

4. The method as recited in claim 3, further comprising normalizing the variations in thoracic impedance.

5. The method as recited in claim 3, further comprising normalizing the variations in thoracic impedance by differentiating the variations.

6. The method as recited in claim 2, wherein the parameter comprises one of chest movements in response to breathing, variations in air pressure in response to breathing, or variations in tidal volume in response to breathing.

7. The method as recited in claim 2, wherein determining a value for each ventilation cycle comprises determining a valley-to-peak magnitude for each ventilation cycle, wherein a respiratory expiration comprises a valley and a respiratory inspiration comprises a peak.

8. The method as recited in claim 2, wherein determining a value for each ventilation cycle comprises calculating a rate of change of the ventilation related parameter at regular intervals and summarizing the calculated rates of change during each ventilatory cycle using a single value.

9. The method as recited in claim 2, wherein the threshold value for filtering the values comprises one of: a mean of the values; an average of the values; a moving average of the values; a standard deviation from the mean for the values; a multiple of a standard deviation from the mean for the values; or a value derived from medical definition of apnea.

10. The method as recited in claim 9, further comprising measuring a time interval between two of the centroids.

11. The method as recited in claim 9, wherein diagnosing apnea as a function of the centroid comprises measuring a time interval between two of the centroids and diagnosing apnea based on the time interval.

12. The method as recited in claim 1, further comprising recomputing the one or more of the centroids at regular intervals.

13. The method as recited in claim 12, wherein the regular interval is daily.

14. The method as recited in claim 12, further comprising tracking the patient's health based on changes in the centroids due to the recomputing.

15. The method as recited in claim 1, further comprising performing the method in real-time.

* * * * *